United States Patent [19]

Higham et al.

[11] Patent Number: 5,093,319

[45] Date of Patent: Mar. 3, 1992

[54] USE OF DERIVATIVES OF CHITIN SOLUBLE IN AQUEOUS SOLUTIONS FOR PREVENTING ADHESIONS

[75] Inventors: Paul A. Higham, Ringwood, N.J.; Jessica D. Posey-Dowty, Kingsport, Tenn.

[73] Assignee: Pfizer Hospital Products Group, Inc., New York, N.Y.

[21] Appl. No.: 644,758

[22] Filed: Jan. 24, 1991

Related U.S. Application Data

[63] Continuation of Ser. No. 429,687, Oct. 31, 1989, abandoned.

[51] Int. Cl.$^5$ ....................... A61K 31/73; A61L 15/16
[52] U.S. Cl. ....................... 514/55; 514/953; 514/955; 514/944; 536/20; 424/423; 424/444
[58] Field of Search ............... 514/55, 953, 955, 944; 536/20, 55.3; 424/444, 423

[56] References Cited

U.S. PATENT DOCUMENTS

| | | | |
|---|---|---|---|
| 2,040,880 | 5/1936 | Rigby | 18/54 |
| 3,632,754 | 1/1972 | Balassa | 424/180 |
| 4,326,532 | 4/1982 | Hammar | 514/56 |
| 4,378,017 | 3/1983 | Kosugi et al. | 424/35 |
| 4,532,134 | 7/1985 | Malette et al. | 514/55 |
| 4,572,906 | 2/1986 | Sparkes et al. | 514/21 |
| 4,603,695 | 8/1986 | Ikada et al. | 128/334 R |
| 4,619,995 | 10/1986 | Hayes | 536/20 |
| 4,659,700 | 4/1987 | Jackson | 514/55 |
| 4,889,722 | 12/1989 | Sheffield | 424/78 |

FOREIGN PATENT DOCUMENTS

WO86/00912 2/1986 PCT Int'l Appl. .
WO87/07618 12/1987 PCT Int'l Appl. .
2026516 6/1979 United Kingdom .

OTHER PUBLICATIONS

Shigehiro Hirano & Ryuji Yamaguchi, "N-Acetyl-chitosan Gel: A Polyhydrate of Chitin", 1976, pp. 1685–1691.

*Primary Examiner*—Johnnie R. Brown
*Assistant Examiner*—Everett White
*Attorney, Agent, or Firm*—Peter C. Richardson; Lawrence C. Akers; Raymond W. Augustin

[57] ABSTRACT

A method for preventing adhesion between vital tissues includes the step of placing between the tissues a material made up of biodegradable derivatives of chitin which are soluble in aqueous solutions containing dilute acids such as acetic acid. This material has the advantage of requiring no reoperation for its removal since it would be degraded and absorbed after completing its function in vivo. These materials may be in the form of a visco-elastic fluid, a gel, a film or a membrane.

25 Claims, No Drawings

USE OF DERIVATIVES OF CHITIN SOLUBLE IN AQUEOUS SOLUTIONS FOR PREVENTING ADHESIONS

This is a continuation of application Ser. No. 429,687, filed on Oct. 31, 1989, now abandoned.

FIELD OF THE INVENTION

This invention relates to an adhesion preventive. More particularly it relates to a biocompatible material which is useful in surgical operations for preventing adhesions of vital tissues such as skin, blood vessels or organs.

DESCRIPTION OF THE PRIOR ART

Vital tissues such as blood vessels or organs including kidney, liver and intestines are coated with mucous membranes or serous membranes so that they can function independently of each other. Examples of these mucous or serous membranes are the body wall pleura and organ pleura in the thoracic cavity and the parietal peritoneum and mesentery in the abdominal cavity, each protecting the corresponding organs. Surgical operations or inflammation in those portions of the body coated with serous membranes could result in adhesion regardless of the size of the affected part. Such adhesion between vital tissues may be observed not only in particular portions of the body but in all vital tissues. Adhesion between vital tissues has heretofore presented a serious problem in the surgical field.

In the field of orthopedics, conditions such as acute or chronic arthritis such as suppurative, rheumatoid arthritis, gonorrheal, tuberculous or traumatic injuries at a joint, such as fracture or sprain, would result in ankylotic diseases wherein the surface of the bones constituting the joint adhere to each other and thereby restrict the mobility of the joint. Congenital radioulnar synostosis wherein a spoke bone and an ulna adhere together is difficult to remedy by a surgical operation, since the separated bones would frequently re-adhere.

As described above, adhesion of vital tissues, large or small, may be observed in most surgical fields. Adhesion could occur for various reasons including mechanical and chemical stimulations of vital tissues accompanying surgical operations, postoperative bacterial infection, inflammation or complications. Consequently, it is necessary to prevent postoperative adhesion between vital tissues.

Conventional adhesion preventives such as liquid paraffin, camphor oil, chondroitin sulfate and urea exhibit an insufficient effect since they function only temporarily. On the other hand, synthetic polymer membranes such as gutta percha or poly(tetrafluoroethylene), which have been used for preventing postoperative adhesion at portions of the body where there is a fear of adhesion setting in, would remain in the body as foreign bodies. Therefore, it is necessary to take out the used membrane by reoperation.

Consequently, there has been a long felt need to find ways to prevent adhesions after surgery. Others have addressed the problem of adhesion prevention utilizing biodegradable materials. U.S. Pat. No. 4,603,695 which issued on Aug. 5, 1986 to Ikada et al refers to the use of an absorbable polyester polymer. This patent also mentions, in passing, the use of chitin. This material can be absorbed by hydrolysis in vivo.

Chitin and chitosan (partially deacetylated chitin) are well known biocompatible materials whose preparation has been described in U.S. Pat. No. 2,040,880 which issued on May 19, 1936. A derivative of chitosan, N,O-carboxymethyl chitosan, and its production has been described in U.S. Pat. No. 4,619,995 which issued on Oct. 28, 1986 to E.R. Hayes.

Uses of chitin and other polysaccharides for wound healing or adhesion prevention purposes are referred to in U.S. Pat. Nos. 3,632,754, 4,532,134, 4,659,700, 4,572,906, 4,378,017, British Patent 2026516, European Patent 200574 and PCT publications WO 86/00912, WO 87/07618 (PCT/US87/01246). None of these patents or publications, however, teach a simple way of forming films and gels from derivatives of chitin which are soluble in aqueous solutions.

SUMMARY OF THE INVENTION

It is an object of this invention to provide a biodegradable, absorbable material capable of preventing adhesions.

It is another object of this invention to provide a material for prevention of adhesions which can form a visco-elastic fluid by temporarily being cross-linked by non-toxic ionic bridges which will begin to degrade after a predetermined time period.

It is yet an additional object of the invention to provide a material for preventing adhesions which can be made from biocompatible material which can be easily made into a flexible film, a gel or a membrane having a gel core and can be easily and safely applied during surgery performed on humans or other mammals.

Accordingly, these and related objects are achieved by a preferred method which includes placing a material comprising biodegradable derivatives of chitin, which are soluble in dilute acidic aqueous solutions, between the tissues in order to prevent adhesions.

One adhesion prevention material of the present invention is an aqueous hydrogel polymer which dissolves over time in vital tissues. Since this material already contains water in order to obtain the desired properties, later hydrolysis is unnecessary. In the past, hydrogels have been used but they have either been covalently cross-linked to improve their life, and therefore have undesirably long degradation times, or else they did not last long enough in the site to be effective. The adhesion prophylaxis of the present invention comprises a polymer which is biocompatible and biodegradable comprised of polysaccharide units which may be broken down by the body into simple sugars which are then metabolized. The half life of the hydrogel material to be used in adhesion prevention can range from about 2-3 days to up to about one year in vivo. Therefore, it is possible to prevent adhesion by placing the adhesion preventative at that portion of the body of a warm blooded mammal undergoing surgery where there is a fear of adhesion setting in. The period the prophylaxis stays in place depends on the rate of absorption by dissolution or by degradation. The adhesion preventative made of the material of the present invention will disappear without requiring reoperation for its removal.

In one preferred embodiment the derivative of chitin is N,O CM-chitosan, and a second preferred derivative of chitin is chitosan. Other preferred derivatives of chitin are N, CM-chitosan; O, CM-chitosan; sulfated N, CM-chitosan and CM-chitin.

The preferred method may further comprise the step of forming a gel prior to placing the material between the tissue by dissolving a maximum of 4% by weight of the derivative of chitin in the aqueous solution. The step of mixing an anti-thrombogenic agent with the soluble biodegradable derivative of chitin prior to placing the material between the tissues may be included. In the preferred method the aqueous solution contains acetic acid.

In another embodiment the method for preventing adhesions between vital tissues comprises the steps of dissolving a member selected from the group consisting of chitosan; N, CM-chitosan; N,O CM-chitosan; O, CM-chitosan, or combinations thereof, in an aqueous solution; then drying the solution so as to form a film. The film is then cross-linked with an aqueous solution containing a cross-linking agent and a visco-elastic fluid is formed by dissolving the film in a hot aqueous solution. The visco-elastic fluid is then placed between vital tissues to prevent adhesions. In this method sulfuric acid is one suitable cross-linking agent with the concentration of sulfuric acid being less than 0.5 molar. In this embodiment another suitable cross-linking agent is a member selected from the group consisting of aspartic acid, glutamic acid, corresponding salts of these acids, or combinations thereof wherein the wetting solution is saturated with the cross-linking agent.

Alternately the cross-linking may be performed using an aqueous solution having a concentration of cross-linking agent such that cross-linking occurs prior to the film dissolving under the action of the wetting solution.

In yet another embodiment the method for preventing adhesions between vital tissues comprises the steps of dissolving a member selected from the group consisting of chitosan; CM-chitosan; N, CM-chitosan; N,O CM-chitosan; O, CM-chitosan and a combination thereof in an aqueous solution. The solution is then dried so as to form a film. A closed membrane is then formed surrounding a visco-elastic fluid by placing the film in a cross-linking bath saturated with an amino acid negatively charged at a pH of 6. The membrane enclosing the visco-elastic fluid is then placed between the tissues to prevent adhesion. In this method the amino acids may be selected from the group consisting of aspartic acid, glutamic acids, corresponding salts of these acids, or combinations thereof.

These and other objects and advantages of the present invention will become apparent from the following detailed description which discloses several examples and embodiments of the invention.

DESCRIPTION OF THE PREFERRED EMBODIMENTS

The biodegradable, absorbable hydrogel polymers to be used as an adhesion preventive of the present invention are polymers which revert to the gel and/or fluid state in vivo over time. Examples of these polymer materials include polysaccharides containing amino sugar such as chitosan, or derivatives thereof, or chitin and derivatives thereof. Chitin is a homopolymer of N-acetyl-D-glucosamine consisting of $\beta(2-4)$ linkage and is the major element found in the shells of insects and crustaceans. Chitosan is a partially deacetylated chitin defined for the purposes herein as being greater than 50% deacetylated.

Among these materials it is preferable to use water soluble polymers, which have not been highly cross-linked to form insoluble materials. It has been found advantageous to use those polymers which either can be used un-derivatized as visco-elastic materials or which can be temporarily cross-linked by non-toxic ionic bridges to form substances which will begin to degrade in a period of about 2-5 days up to about one year. In order to vary the degradation time, the thickness of the membrane or film and/or the amount of cross-linking can be varied. Examples of these materials are those illustrated by the following structural formulae I-VI.

I. N-CM-chitosan:

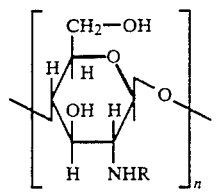

where R is H (18-52% of the time) or R is

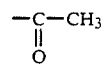

(0-30% of the time) or R is

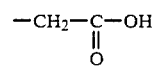

(18-70%) of the time).

II. O-CM-chitosan:

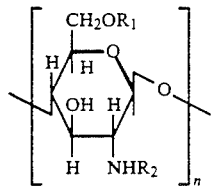

where $R_1$ is H (0-82% of the time) or $R_1$ is

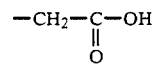

(18-100% of the time) AND $R_2$ is H (50-100% of the time) or $R_2$ is

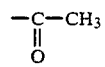

(0-50% of the time).

III. N,O, CM-chitosan:

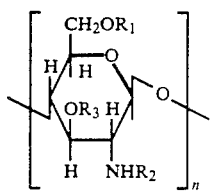

where $R_1$ is H (0-82% of the time) or $R_1$ is $$-CH_2-\underset{\underset{O}{\|}}{C}-OH$$

(18-100% of the time) AND $R_2$ is H (0-60% of the time) or $R_2$ is $$-CH_2-\underset{\underset{O}{\|}}{C}-OH$$

(18-100% of the time) or $R_2$ is $$-\underset{\underset{O}{\|}}{C}-CH_3$$

(0-40% of the time) AND $R_3$ is H (0-100% of the time) or $R_3$ is $$-CH_2-\underset{\underset{O}{\|}}{C}-OH$$

(0-50% of the time).

IV. chitin:

$$\left[\begin{array}{c} CH_2OH \\ \text{(ring structure)} \\ H \quad NHR \end{array}\right]_n$$

where R is H (0-40% of the time) or R is $$-\underset{\underset{O}{\|}}{C}-CH_3$$

(60-100% of the time).

V. Chitosan:

$$\left[\begin{array}{c} CH_2OH \\ \text{(ring structure)} \\ H \quad NHR \end{array}\right]_n$$

where R is H (50-100% of the time) or R is $$-\underset{\underset{O}{\|}}{C}-CH_3$$

(0-50% of the time).

VI. CM-chitin:

$$\left[\begin{array}{c} CH_2OH \\ \text{(ring structure)} \\ H \quad NHR \end{array}\right]_n$$

where R is H (0-30% of the time) or R is $$-CH_2-\underset{\underset{O}{\|}}{C}-OH$$

(18-70% of the time) or R is $$-\underset{\underset{O}{\|}}{C}-CH_3$$

(0-82% of the time).

Examples of polymers represented by the above formulas include: chitosan acetate chitosan lactate; chitosan sulfate; chitosan glutamate; methyl-chitosan; N, carboxyl methyl-chitosan; O, carboxyl methyl-chitosan; N,O carboxyl ethyl-chitosan; N, carboxyl ethyl-chitosan; O, carboxyl ethyl-chitosan; N,O- carboxyl propyl-chitosan; N- carboxyl propyl chitosan; O-carboxyl ethyl- chitosan; cross-linked chitosan or derivatives thereof, and carboxyl alkyl chitins such as carboxymethyl chitin, carboxyethyl chitin and carboxypropyl chitin.

These polymers are prepared from natural products or by fermentation methods and are all commercially available. The molecular weight of these biodegradable polymers for use in the present invention preferably can range from about 1,000 Daltons to about 5,000,000 Daltons. Gels may be formed by dissolving up to 4% by weight of the derivative of chitin in the aqueous solution.

When using a membrane, film or sheet polymer, it is preferable to use polymer films or woven sheets which break down into visco-elastic materials. Non-limiting examples of these are chitosan acetate or chitosan lactate films cross-linked with sulfate, phosphate, or borate anions or carboxyl methyl-chitosan (CM-chitosan) cross-linked with glutamic acid or aspartic acid, or salts thereof such as chitosan glutamate. All of these films break down by ion exchange or other mechanisms to form gel materials which are then much more easily removed from the site. The rate of breakdown is a function of the rate of exchange of the non-toxic cross-linking agent with its environment.

Also it is possible to prevent adhesions by injecting a visco-elastic material which is more viscous and elastic than blood so that it prevents blood from clotting at the interface of two vital tissues, thus preventing an adhesion from forming. These materials include chitosan and its derivatives, and water soluble chitin materials. Some of these materials can be lightly complexed or cross-linked ionically to form a thicker more viscoelastic substance. The present invention can be heat sterilized, filter sterilized, or possibly radiation sterilized, depending on the application. In addition, an anti-thrombogenic agent, such as heparin or the like, can be mixed with the derivative of chitin prior to placing the material between the vital tissues.

The invention will now be described in further detail with reference being made to the following examples. It should, however, be recognized that the examples are given as being illustrative of the present invention and are not intended to define the spirit and scope thereof.

EXAMPLE 1

A. One gram of medical grade chitosan (free amine), such as Protan, Inc.'s Protosan LV Chitosan acetate, was added to 44 ml of a 2% acetic acid solution and shaken, stirred or mixed until dissolved. Any insoluble matter was removed. The viscosity of the solution was greater than 250 cps as measured by a Brookfield viscometer. The solution was then poured and allowed to dry to make clear films.

B. Films were ionically cross-linked by placing the film of a measured thickness into dilute solutions of sulfuric acid, or sodium sulfate. It was necessary to use stronger concentrations of $SO_4^-$ ions to cross-link thin films. The cross-linking or insolubilizing reaction had to occur before the soluble chitosan film had a chance to dissolve.

Films of thicknesses $\geq 0.04$ mm cross-linked easily when placed in 0.024 M sulfuric acid and became elastic and flexible.

Films of thicknesses $\leq 0.04$ mm cross-linked in 0.24 M sulfuric acid and became elastic and flexible.

EXAMPLE 2

The same procedure was used to make films as in Example I A. However, instead of using dilute sulfuric acid solutions, sodium sulfate, sodium phosphate or sodium borate solutions at a pH of less than or equal to 6 were used to cross-link the dry chitosan acetate films.

The concentration of sodium sulfate solutions used was 0.5 M for films between 0.024-0.1 mm thick. Similarly, 0.5 M sodium phosphate, phosphoric acid (10%) and monohydrogen orthophosphate, were used to cross-link films of these thicknesses as was sodium borate, $Na_2B_2O_7$, at less than 0.4 M concentration.

The elastic moduli of the films ranged between 13-31 pascals when wet.

EXAMPLE 3

2.0 grams of chitosan (medical grade) was dissolved in 100 ml of 0.17 M acetic acid. Any insoluble material was removed. The viscosity of the solution was >250 cps. The solution was poured into a mold and allowed to dry.

Films of thicknesses ranging from 0.04-0.1 mm were cross-linked or insolubilized with 1% $H_2SO_4$ (0.24 M). The thicker films took less time to react than the thin films. The films could be boiled in water for one hour without insolubilizing.

EXAMPLE 4

1 g of N,O CM-chitosan was mixed with 100 ml of deionized water. Films were made by pouring this solution onto a flat surface and allowing it to evaporate. The dry films were then placed in a saturated solution of glutamic acid at room temperature to cross-link them.

Thin ($\leq 0.5$ mm thick) films readily cross-linked ionically to form thin slightly elastic films. Thick films (0.8 mm in thickness or more) formed a cross-linked outer surface with gelatinous material in the interior.

EXAMPLE 5

The same types of films were made by adding the films to a saturated solution of aspartic acid rather than glutamic acid as in the above example. The properties of the materials made with aspartic acid rather than glutamic acid did not differ noticeably.

EXAMPLE 6

2 grams of N,O CM-chitosan were added to 100 ml of water. The solution was mixed well. The solution was poured and dried into a small mold to make a thick N, O, CM-chitosan film and then cross-linked using saturated solutions of aspartic acid, glutamic acid or a combination thereof. These acids were negatively charged at a pH of 6 ie. were acidic amino acids which contain a carboxylic acid group in the R group end of the amino acid and therefore ionize to become an anion at pH $\geq 6$. The sample formed a pillow structure having an outer film or membrane. The membrane formed because only the outside of the film had cross-linked and the inside remained visco-elastic. When the pillow structure was placed in boiling water, the structure of the film resorbed into a thick visco-elastic substance. The total percentage of CM-chitosan in the solution was less than 0.25%.

EXAMPLE 7

2 grams of chitosan acetate were added to 0.9% NaCl and mixed. After heat sterilization in the absence of oxygen, the material was then ready to be injected into place.

EXAMPLE 8

A 2% N,O CM-chitosan was added to 900 ml of 0.9% NaCl. The solution could be used as a visco-elastic substance to inject at the site in order to prevent adhesions from forming.

While acetic acid was used to solubilize the chitin or derivatives thereof, other well known acids in concentrations capable of solubilizing the chitin may also be used.

While several examples of the present invention have been described, it is obvious that many changes and modifications may be made thereunto, without departing from the spirit and scope of the invention.

We claim:

1. A method of preventing adhesions between soft internal body tissues consisting essentially of the step of placing a material between the tissues, said material comprising biodegradable ionically cross-linked carboxy containing derivatives of chitin which are soluble in dilute acidic aqueous solutions.

2. The method as set forth in claim 1 wherein the derivative of chitin is N,O carboxyl methyl-chitosan.

3. The method as set forth in claim 1 wherein the derivative of chitin is chitosan.

4. The method as set forth in claim 1 wherein the derivative of chitin is N, carboxyl methyl-chitosan.

5. The method as set forth in claim 1 wherein the derivative of chitin is O, carboxyl methyl-chitosan.

6. The method as set forth in claim 1 wherein the derivative of chitin is sulfated N, carboxyl methyl-chitosan.

7. The method as set forth in claim 1 wherein the derivative of chitin is carboxyl methyl-chitin.

8. The method as set forth in claim 1 wherein the aqueous solution contains acetic acid.

9. A method for preventing adhesions between soft internal body tissues which comprises the steps of:
dissolving a member selected from the group consisting of chitosan; N, carboxyl methyl-chitosan; N,O carboxyl methyl-chitosan; O, carboxyl methyl-chitosan and combinations thereof, in a dilute acidic aqueous solution;
drying the solution so as to form a film;
cross-linking the film by wetting it with an aqueous acidic solution having an anion capable of ionically cross-linking with amino groups of said dissolved member;
forming a visco-elastic fluid by dissolving the film in an aqueous solution; and
placing the visco-elastic fluid between soft internal body tissues to prevent adhesions.

10. The method as set forth in claim 9 wherein a sulphate anion of sulfuric acid ionically cross-links with said amino group.

11. The method as set forth in claim 10 wherein the concentration of sulfuric acid is less than 0.5 molar.

12. The method as set forth in claim 9 wherein the anion is provided by a member selected from the group consisting of aspartic acid, glutamic acid, corresponding salts of these acids or combinations thereof.

13. The method as set forth in claim 12 wherein the aqueous solution is saturated with the anion providing acidic solution.

14. The method as set forth in claim 9 wherein the cross-linking is performed using an aqueous solution having a concentration of cross-linking agent such that cross-linking occurs prior to the film dissolving under the action of the wetting solution.

15. A method for preventing adhesions between soft internal body tissues which comprises the steps of:
dissolving a member selected from the group consisting of chitosan; carboxyl methyl-chitosan; N, carboxyl methyl-chitosan; N,O carboxy methyl-chitosan; O, carboxy methyl-chitosan and combinations thereof in an aqueous solution;
drying the solution so as to form a film;
forming a closed film surrounding a visco-elastic fluid by placing the film in an ionic cross-linking bath saturated with an amino acid negatively charged at a pH of 6; and
placing the film enclosing the visco-elastic fluid between the tissues to prevent adhesion.

16. The method as set forth in claim 15 wherein the amino acids are selected from the group consisting of aspartic acid, glutamic acids, corresponding salts of these acids, or combinations thereof.

17. A method for preventing adhesions between soft internal body tissues which comprises the steps of:
dissolving biodegradable carboxy containing derivatives of chitin in a dilute acidic aqueous solution;
drying the solution so as to form a film;
cross-linking the film by wetting it with an acidic aqueous solution having an anion capable of ionically cross-linking with amino groups of said derivatives of chitin;
forming a visco-elastic fluid by dissolving the cross-linked film in an aqueous solution; and
placing the visco-elastic fluid between soft internal body tissues to prevent adhesions.

18. The method as set forth in claim 17 wherein the sulphate anion of sulfuric acid ionically cross-links with said amino groups.

19. The method as set forth in claim 18 wherein the concentration of sulfuric acid is less than 0.5 molar.

20. The method as set forth in claim 17 wherein said anion is provided by an amino acid selected from the group consisting of aspartic acid, glutamic acid, corresponding salts of these acids or combinations thereof.

21. The method as set forth in claim 20 wherein the aqueous solution is saturated with the cross-linking agent.

22. The method as set forth in claim 17 wherein the cross-linking is performed using an aqueous solution having a concentration of cross-linking agent such that cross-linking occurs prior to the film dissolving under the action of the wetting solution.

23. A method for preventing adhesions between soft internal body tissues which consists essentially of:
dissolving biodegradable carboxy containing derivatives of chitin in a dilute acidic aqueous solution;
drying the solution so as to form a film;
cross-linking the film by wetting it with an acidic aqueous solution having an anion capable of ionically cross-linking with amino groups of said derivatives of chitin;
forming a visco-elastic fluid by dissolving the cross-linked film in an aqueous solution;
placing the visco-elastic fluid between soft internal body tissues to prevent adhesions; and
mixing an anti-thrombogenic substance with the film after cross-linking the film.

24. A method of preventing adhesions between soft internal body tissues consisting essentially of the steps of placing a material between the tissues, said material consisting essentially of biodegradable carboxy containing derivatives of chitin which are soluble in dilute acidic aqueous solutions; and
said material being formed into a gel by ionic cross-linking prior to placing the material between the tissue by dissolving a maximum of 4% by weight of the derivative of chitin in an aqueous acidic solution.

25. A method of preventing adhesions between soft internal body tissues consisting essentially of the step of placing a material between the tissues, said material consisting essentially of ionically cross-linked carboxy containing biodegradable derivatives of chitin which are soluble in dilute acidic aqueous solutions and wherein said material is mixed with an anti-thrombogenic agent with the soluble biodegradable derivative of chitin prior to placing the material between the tissues.

* * * * *